(12) United States Patent
Bieger et al.

(10) Patent No.: US 6,768,496 B2
(45) Date of Patent: Jul. 27, 2004

(54) SYSTEM AND METHOD FOR GENERATING AN IMAGE FROM AN IMAGE DATASET AND A VIDEO IMAGE

(75) Inventors: Johannes Bieger, Erlangen (DE); Rainer Graumann, Hoechstadt (DE); Norbert Rahn, Forchheim (DE)

(73) Assignee: Siemens Aktiengesellschaft, Münich (DE)

( * ) Notice: Subject to any disclaimer, the term of this patent is extended or adjusted under 35 U.S.C. 154(b) by 232 days.

(21) Appl. No.: 09/822,616

(22) Filed: Mar. 30, 2001

(65) Prior Publication Data

US 2001/0035871 A1 Nov. 1, 2001

(30) Foreign Application Priority Data

Mar. 30, 2000 (DE) .......................................... 100 15 826

(51) Int. Cl.[7] .................................................. G09G 5/12
(52) U.S. Cl. ........................ 345/630; 348/65; 348/567; 600/407
(58) Field of Search ................................ 345/592, 629, 345/630, 631, 632, 633, 641; 348/65, 77, 565, 567, 588; 600/407, 595, 676; 725/10, 21

(56) References Cited

U.S. PATENT DOCUMENTS 5,776,050 A * 7/1998 Chen et al. .................. 600/117
5,912,720 A * 6/1999 Berger et al. ............... 351/206
6,139,183 A 10/2000 Graumann

FOREIGN PATENT DOCUMENTS

DE 40 21 102 1/1991
DE 198 00 765 4/1999

OTHER PUBLICATIONS

"Lexikon der Computergrafik und Bildverarbeitung," Iwainsky et al., (1994) pp. 30–32.

* cited by examiner

Primary Examiner—Michael Razavi
Assistant Examiner—Thu-Thao Havan
(74) Attorney, Agent, or Firm—Schiff Hardin LLP

(57) ABSTRACT

In a system and a method for generating an image that contains superimposed or fused image data, a first system acquires an image dataset from a subject and a second system obtains a video image of the subject. The positions of the first, the second systems in the acquisition of the image datasets are determined with the an arrangement for position determination, such as a navigation system, with reference to which the position of the image dataset acquired with the first system and the position of the video image dataset can be determined in space, so that the two image datasets can be superimposed or fused with one another. An arrangement also can be provided for generating a video image expanded with image data of the image dataset acquired with the first system.

17 Claims, 2 Drawing Sheets

SYSTEM AND METHOD FOR GENERATING AN IMAGE FROM AN IMAGE DATASET AND A VIDEO IMAGE

BACKGROUND OF THE INVENTION

1. Field of the Invention

The present invention is directed to a system and to a method for generating an image that contains superimposed or fused image data, having a first system for acquiring an image dataset of a subject and second system for registering a video image of the subject.

2. Description of the Prior Art

Given minimally invasive surgical interventions, for example in endoscopy or laparoscopy wherein medical instruments are introduced into the body of a life form to be treated via small openings, the attending surgeon usually has no direct view of the operating field. Direct view of the operating field is therefore replaced in such surgical interventions by a video imaging of the operating field, this usually ensuing with optical means integrated into an endoscope, a laparoscope or a catheter. In contrast to a direct view of the operating field, the viewing conditions in the video imaging are significantly limited.

An improvement of the view is achieved when, given minimally invasive interventions, the endoscope, the laparoscope or the catheter or, respectively, the respective optical system thereof is pivoted for image registration. Further, the view of the operating field can be improved by increasing the distance of the optical system from the subject to be imaged.

Another approach for expanding the field of vision of a physician is disclosed in U.S. Pat. No. 5,912,720 for the treatment of eye maladies wherein the superimposition of stored optical or angiographic images of a subject with one or more optical images of the subject acquired in real time ensues. The superimposition of the images is thereby based on a registration of anatomical landmarks, i.e. specific anatomical peculiarities of the registered tissue that are imaged in the images to be superimposed on one another and serve as a point of reference for the superimposition.

German OS 198 00 765 discloses a method and a system for generating image presentations of the surface of the inside wall of hollow bodies within the framework of an endoscopy examination, particularly of cavity organs and vessels. A number of individual frames of different regions of the inside wall of the hollow body to be examined are registered with the endoscope. The video image signals are digitized and, based on the digitized video image signals, a superimposition or combining of the individual frames to form an overall image is undertaken in an image processing device.

U.S. Pat. No. 5,776,050 discloses supplementing a video image acquired with an endoscope with topological image data of a 3D image data set stored in a computer to form an image expanded by the topological image data. The position of the endoscope in a coordinate system different from the coordinate system of the 3D image dataset is thereby determined with a navigation system. In order to produce a relationship between the two coordinate systems, and thus the 3D image dataset and the video image data, so that a superimposition of the video image data with the topological image data is possible, a registration procedure, for example on the basis of anatomical landmarks, is implemented. Subsequently, video images supplied by the endoscope, due to the continuous positional acquisition of the endoscope by the navigation system and the transformation rule between the coordinate system determined by the registration, can be continuously supplemented with topological data to form an expanded image that increases the field of vision.

A disadvantage of this procedure, however, is that the required registration procedure is time-consuming and susceptible to error and is therefore difficult to integrate into a routine execution during the course of a minimally invasive surgical intervention.

In the section "Bildrektifikation", methods for geometrical and radiometric correction of picture elements for the purpose of matching two images are described in the "Lexikon der Computergrafik und Bildverarbeitung" by Iwainsky, A. and Wilhelmi W., Vieweg Verlagsgesellschaft, 1994, pages 31, 32. Two methods for geometrical correction are described, one directed to the calculation of two-dimensional correction polynomials of the order k and the other is directed to a perspective transformation method.

German OS 40 21 102 discloses a medical diagnostic installation having two integrated, imaging systems, one being an x-ray system and the other being an ultrasound system. With the assistance of position sensors, the surface or the spatial allocation of an ultrasound tomogram generated with the ultrasound system with respect to the x-ray image generated by the x-ray system is determined in order to be able to mix the ultrasound tomogram into the x-ray image. To this end, the x-ray system and the ultrasound system, however, must be arranged in a defined way relative to one another in order to be able to produce a relationship between the image data of the x-ray system and of the ultrasound system.

Moreover, German OS 197 46 092 discloses an x-ray registration device in the form of a C-arm x-ray apparatus for acquiring a 3D image dataset. The 3D image dataset is generated from a series of 2D projections that are acquired successively from different projection directions relative to a subject. In order to be able to acquire such a 3D image dataset from 2D projections, however, knowledge of the projection geometries is required, i.e. the exact knowledge of the position of the x-ray source and of the x-ray receiver as well as of the projection angle during each and every individual 2D projection. In order to determine these positions, the C-arm x-ray apparatus has transmission devices arranged at the x-ray source and at the x-ray receiver and has reception devices stationarily arranged relative thereto, for example in the form of ultrasound transmitters and receivers.

SUMMARY OF THE INVENTION

An object of the present invention is to provide a system and a method of the type initially described wherein a superimposition or fusion of, for example, image data non-evasively acquired from the inside of a subject and video image data can ensue for producing an image without a registration procedure.

According to the invention, this object is achieved in a system for generating an image that contains superimposed or fused image data, having a first system for acquiring an image dataset from a subject, a second system for the registration of a video image of the subject, means for determining the position of the first system in the acquisition of the image dataset and the position of the second system in the registration of the video image, a unit for determining the position of the image dataset acquired with the first system and the position of the video image acquired with the second system, a unit for superimposition or fusion of image data of the respective image datasets acquired with the first and second systems, and a unit for generating an image from the superimposed or fused image data. In the invention, therefore, the position of the first system in the acquisition of the image dataset as well as the position of the second system in the registration of a video image are identified in a reference coordinate system, so that the position of the first and second systems relative to one another is known. Due to the registration parameters that are likewise known, the position of the image dataset acquired with the first system can be determined on the basis of the known positions of the first system in the acquisition of an image dataset. Due to the registration parameters that are likewise known, the position of the image plane of the video image in the reference coordinate system can be determined on the basis of the known position of the second system in the registration of the video image. Therefore, image data of the image dataset acquired with the first system and the video image data can be superimposed on one another or fused with one another. In this way, for example in minimally invasive medical interventions, intra-operative images can be produced without a registration procedure for producing a spatial relationship between the image data of the image dataset acquired with the first system and the video image data, said intra-operative images containing video image data and, for example, non-invasively acquired image data from the inside of the subject. Video images are preferably produced that are supplemented by the non-invasively acquired image data of the image dataset produced with the first system, so that the possibly limited field division of a video image is expanded. The video image data are, for example, supplemented by image data from the image plane of the image dataset corresponding to the image plane of the video image. The presentation of the generated images can, for example, ensue as a picture-in-picture display.

In a preferred embodiment of the invention the unit for determining the positions of the first and of the second systems also can determine the position, i.e. the attitude and orientation, of the subject in space. In this way, for example given minimally invasive medical interventions, non-invasively, pre-operatively acquired image data of the subject also can be employed for superimposition or fusion with video image data registered during the minimally invasive surgical intervention. As a result of the acquisition of the position of the subject in the pre-operatively undertaken registration of an image dataset with the first system and as a result of the acquisition of the position of the subject during the implementation of the actual surgical intervention at the subject, modifications in the position of the subject can be taken into consideration and the image dataset can be brought into agreement with respect to its attitude in space with the modified attitude of the subject, or can be adapted to the modified attitude of the subject. Moreover, the determination of the position of the subject is also meaningful when the subject to be examined moves or is moved during the intervention between the acquisition of the image dataset with the first system and the registration of the video image. Accordingly, the subject is in a different attitude in the image dataset acquired with the first system than in the registration of the video image with the second means. By acquiring the movements of the subject, however, it is possible—taking the movements of the subject into consideration—to bring the image dataset acquired with the first system into agreement with the new attitude of the subject, so that a video image registered given the new attitude of the subject can be unproblemmatically superimposed or fused with image data of the adapted image dataset.

In a version of the invention, the unit for determining the positions of the first and of the second systems is a navigation system. The navigation system includes an arrangement for non-contacting determination of the position of a subject. The navigation system can, for example, be a known optical navigation system, an electromagnetic navigation system, a navigation system based on ultrasound or of some other known navigation system that is known in and of itself.

In a preferred embodiment of the invention a 3D image dataset is acquired with the first system. The first system can be an x-ray system, preferably a C-arm x-ray system, or an ultrasound system, and the second system can be an endoscope, a laparoscope or a catheter. The advantage of employing a C-arm x-ray system or an ultrasound system for non-invasive acquisition of an image dataset is a relatively economical generation of the image datasets compared to the acquisition of datasets with an x-ray computed tomography apparatus or a magnetic resonants apparatus.

The above also is achieved in a method for generating an image that contains superimposed or fused image data, having the following method steps:

a) Acquiring an image dataset of a subject with a first system for acquiring image data;

b) Registration of a video image of the subject with a second system;

c) Determination of the position of the first system in the acquisition of the image dataset and the position of the second system in the registration of the video image;

d) Determining the position of the image dataset acquired with the first system and the position of the video image registered with the second system;

e) Superimposing or fusing image data of the first image dataset acquired with the first system and image data of the video image registered with the second system; and f) Generating an image from the superimposed or fused image data.

In the inventive method, thus, as discussed in conjunction with the inventive system, the position of the image dataset acquired with the first system and the position of the video image registered with the second system relative to one another in a reference coordinate system are identified on the basis of the identified position of the first system in the acquisition of the image dataset and the position of the second system in the registration of the video image with respect to a reference coordinate system. Since, accordingly, the attitude of the image data of the image dataset relative to the attitude of the video image data is known, the image data can be superimposed on one another or be fused with one another. As a result, images can be generated that contain video image data and, for example, non-invasively acquired image data from the inside of a subject.

In a further version of the inventive method, the position of the subject also is identified; the identification of the position of the first and of the second systems as well as the determination of the position of the subject ensues with a navigation system. The employment of a know navigation system represents an especially practical form for determining the positions of the first and second system s as well as the position of the subject.

DESCRIPTION OF THE PREFERRED EMBODIMENTS

Figure 1:
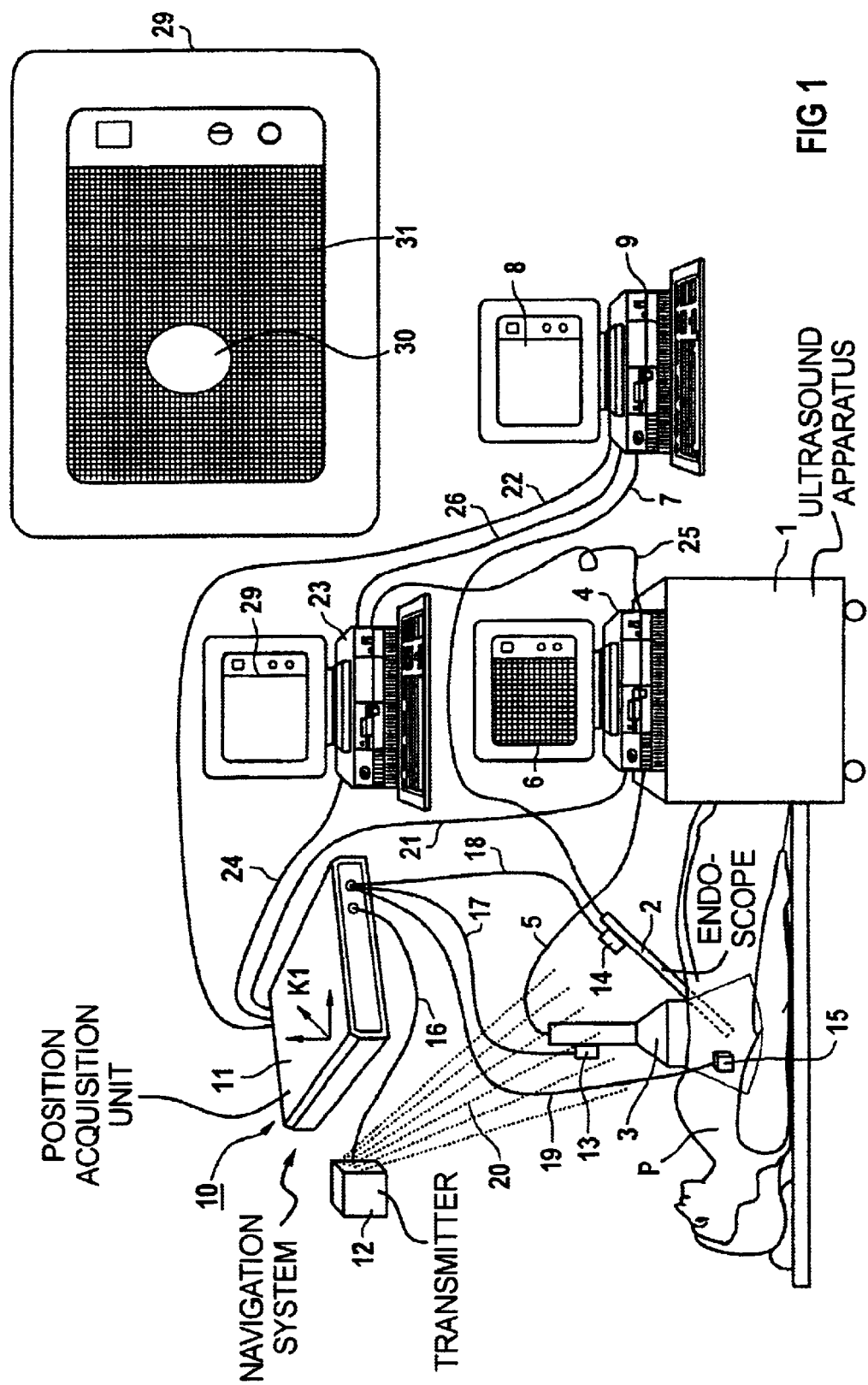
FIG. 1 illustrates an inventive system having a navigation system for the implementation of the inventive method for generating an image that comprises superimposed or fused image data.

The inventive system shown in FIG. 1 is a medical system for minimally invasive surgical interventions in living subjects. The medical system includes a first system for the non-invasive acquisition of an image dataset of a patient P in the form of an ultrasound apparatus 1 and a second system for obtaining a video image from the inside of the body of the patient P in the form of an endoscope 2.

The ultrasound apparatus 1 has an ultrasound head (scanner) 3 that can be applied onto the body surface of the patient P, this being connected by a line 5 to a known image processing unit 4 of the ultrasound apparatus 1. The ultrasound apparatus 1 also has a display 6 connected to the image processing unit 4 in a way that is not shown. In a known way, non-invasive 2D ultrasound images can be acquired from the inside of the body of the patient P with the ultrasound head 3 and can be displayed on the display 6 after image processing by the image processing unit 4 in a way that is not shown. The ultrasound apparatus 1 also allows 3D image datasets of the body tissue of the patient P to be acquired therewith. Such a 3D image dataset is generated in a known way by the image processing unit 4 from a number of ultrasound tomograms registered from different directions and forms the basis for the reconstruction of various 3D ultrasound images.

The endoscope 2, which has penetrated through an opening into the body of the patient in the exemplary embodiment, has known optical means (not shown in greater detail), such as a lens arrangement and an image pickup unit collaborating with the lens arrangement, for example a CCD camera. The video image is registered by the CCD camera are transmitted via a line 7 to a visualization computer 9 provided with a display 8 and can be displayed on the display 8 by the visualization computer 9. A light source, for example a cold light source, that is required for obtaining video images from the inside of the body of the patient P, is not explicitly shown in FIG. 1.

In the exemplary embodiment, the medical system also has an electromagnetic navigation system 10 that with a position acquisition unit 11 in the form of a computer, a transmitter 12 and position sensors 13 through 15 that can be attached to subjects whose position is to be acquired. The position acquisition unit 11 is connected via a line 16 to the transmitter 12 and is connected via lines 17 through 19 to the position sensors 13 through 15. During operation of the navigation system 10, the transmitter 12 generates an electromagnetic field 20 indicated with broken lines in FIG. 1. When the position sensors 13 through 15 of the navigation system 10 are in the electromagnetic field 20, they generate signals from which the position acquisition unit 11 can determine the positions of the position sensors 13 through 15 and, thus, the positions of the subject or object carrying the respective position sensors 13 through 15 in a reference coordinate system K1. The transmitter 12 of the navigation system 10 is thereby arranged in a defined way in the reference coordinate system K1.

In the exemplary embodiment, the position sensor 13 of the navigation system 10 is arranged such in a defined way at the ultrasound head 3 so that not only the position of the ultrasound transmitter and receiver surfaces of the ultrasound head 3 can be identified by the determination of the position of the position sensor 13 in the reference coordinate system K1 defined by the position acquisition unit 11, but also the positions, i.e. the attitudes and orientations, of the image data acquired with the ultrasound head 3 can be determined in the reference coordinate system K1 on the basis of the known registration parameters in the acquisition of ultrasound images.

The position sensor 14 is arranged at the endoscope 2 in a defined way so that, by determining the position of the position sensor 14, the position of the optical lens arrangement of the endoscope 2, and thus of the image plane of a video image obtained by the lens arrangement and the CCD camera, can be determined.

In order to expand the field of vision of a surgeon (not shown in FIG. 1) given minimally invasive interventions at the patient P, that is limited by the video imaging with the endoscope 2, images are generated with the medical system that contain image data of a 3D image dataset acquired with the ultrasound apparatus 1 and image data of the video image acquired with the endoscope 2. At the points in time of the registration of the ultrasound tomograms with the ultrasound apparatus 1 as well as at the points in time of the registration of the video images, the positions of the ultrasound head 3 and the positions of the endoscope 2 are determined by the navigation system 10. The position sensors 13 and 14, respectively arranged at the ultrasound head 3 and at the endoscope 2, are, as already mentioned, disposed in the electromagnetic field 20 of the transmitter 12 indicated with broken lines in FIG. 1, and generate signals from which the position acquisition unit 11 can determine the positions, i.e. the attitudes and orientations, of the ultrasound head 3 and the endoscope 2 with respect to the reference coordinate system K1. The registration of the image data and the determination of the positions of the ultrasound head 3 and the endoscope 2 thereby ensue synchronously, with each position determination being respectively triggered by each image registration. The image processing unit 4 of the ultrasound apparatus 1 and the visualization computer 9 of the endoscope 2 are connected to the position acquisition unit 11 with lines 21, 22.

On the basis of the positions of the ultrasound head 3 in the acquisition of the ultrasound tomograms determined with the navigation system 10, the attitude an orientation of a 3D image dataset generated from the 2D ultrasound tomograms also can be determined in the reference coordinate system K1. In the exemplary embodiment, the generation of the 3D ultrasound image dataset ensues with a superimposition and fusion computer 23 in a known way, the position acquisition unit 11 (via a line 24) and the ultrasound apparatus 1 (via a line 25) being connected thereto. The superimposition and fusion computer 23 receives all position data required for the generation of the 3D image dataset from the position acquisition unit 11 and receives all ultrasound data from the ultrasound apparatus 1. On the basis of the known spatial relationship between the acquired 2D ultrasound image data and the transmission of reception surfaces of the ultrasound head 3, the superimposition and fusion computer 23 can determine the attitude and orientation in the reference coordinate system K1 for each image datum of the generated 3D ultrasound image dataset from which various 3D images of the inside of the body of the patient P can be reconstructed. Accordingly, the attitude and orientation in the reference coordinate system K1 as well as the voxel size, for example in millimeters and degrees, in the reference coordinate system K1 are also known for a 3D image cube arbitrarily reconstructed from the 3D ultrasound image dataset. Alternatively, the generation of the 3D ultrasound image dataset can also ensue with the image processing unit 4 of the ultrasound apparatus 1.

Figure 2:
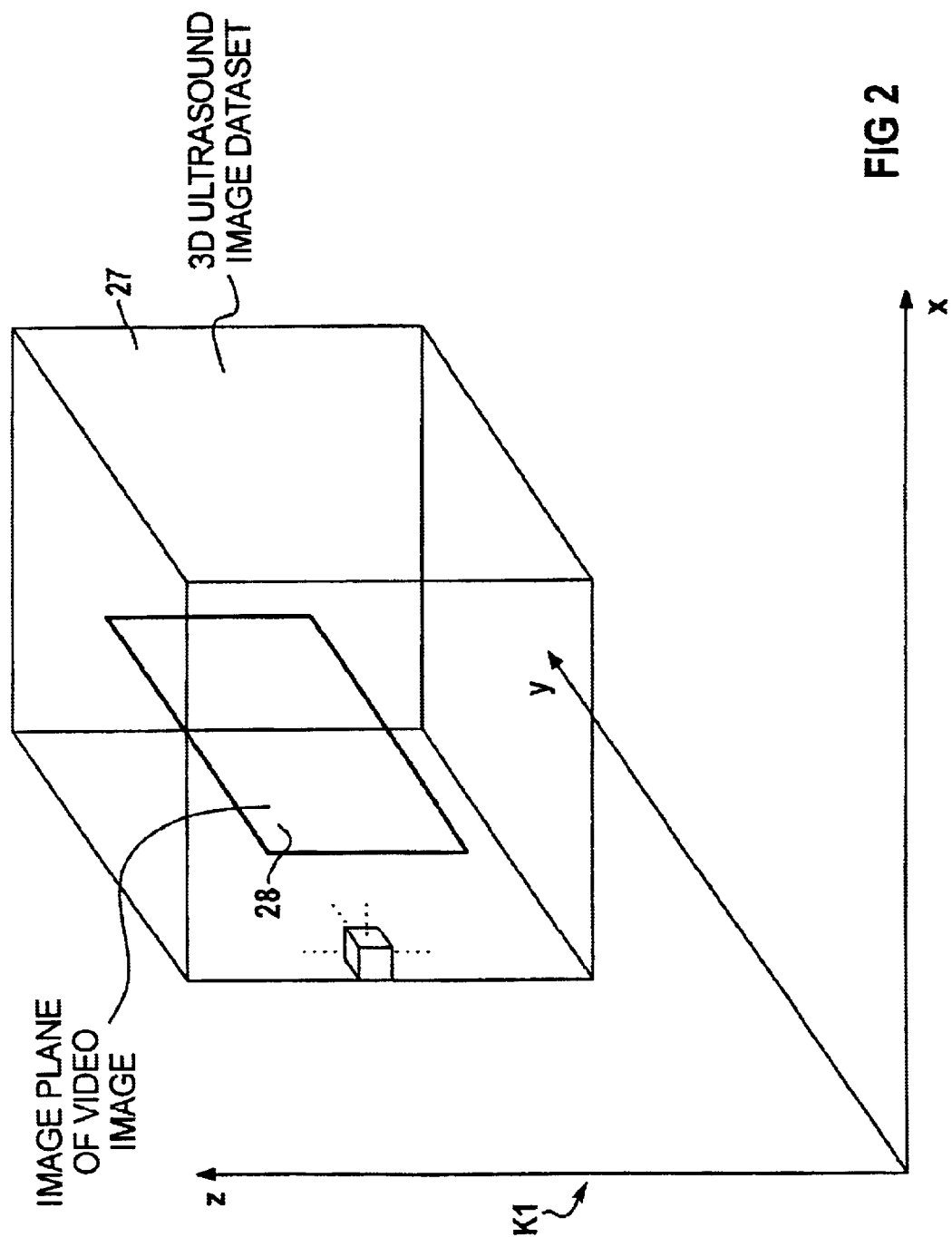
FIG. 2 illustrates the attitude of a 3D image dataset and of an image plane of a video image relative to one another in accordance with the invention.

Since the visualization computer 9 of the endoscope 2 also is connected via a line 26 to the superimposition and fusion computer 23, the superimposition and fusion computer 23 also can determine the positions, i.e. the attitudes and orientations, of the endoscope 2, and thus the image plane of each video image acquired with the endoscope 2 in the reference coordinate system K1 on the basis of the position data of the position acquisition unit 11 as well as on the basis of the setting data transmitted to it and on the basis of the video images of the endoscope 2. As a result of the known positions of the 3D ultrasound image dataset and of the video image dataset, the superimposition and fusion computer 23 operated with appropriate software can superimpose the image data of the 3D ultrasound image dataset and the video image data on one another or fuse them with one another. In a schematic illustration as an example, FIG. 2 shows the position of the 3D ultrasound image dataset indicated with a cube 27 and the position of the image plane 28 of a video image in the reference coordinate system K1.

The fusion of the image data of the 3D ultrasound image dataset with the video image data can be accomplished with known fusion methods, for example alpha blending, as a proportional superimposition. In particular, body tissue can be presented semi-transparently with the assistance of this superimposed presentation. As a result, for example, a view through an organ becomes possible by virtue of ultrasound image data on the other side of an organ shown in the video image being superimposed on the video image. Further, functional information, for example blood flow as well as vessels can be superimposed on the video image. Suitable types of presentations are employed, for example, "perspective surface shaded display" or "perspective volume rendering".

Moreover, the superimposition and fusion computer 23 can generate video images from the superimposed or fused image data that, for example, are supplemented by image data from the plane of the 3D ultrasound image dataset corresponding to the image plane of the video image, these being capable of being presented as picture-in-picture. FIG. 1 shows an enlarged schematic illustration of an image generated from the known image data as a picture-in-picture visualization on a display 29 of the superimposition and fusion computer 23. The video image 30 is thereby supplemented with ultrasound data 31, so that the field of vision of the video image 30 is expanded. Another form of presentation is the side-by-side presentation of the image data, whereby the image data of the 3D ultrasound image data set and video image data are presented in the same orientation and position.

In the superimposition or fusion of the 3D ultrasound image dataset with the video image dataset, usually it will be necessary to adapt (match) the image data to one another in terms of their structure as well. For example, the video image data due to the variable spacing between the endoscope 2 and the tissue to be registered, are present in different scalings compared to the image data of the 3D ultrasound image dataset, and therefore the data must be scaled such that the image data fit to one another. The scaling factor can be identified since the attitude of the endoscope 2 relative to the 3D ultrasound image dataset is known. In the exemplary embodiment, the scaling is undertaken by the superimposition and fusion computer 23.

Further parameters for the image presentation such as the attitude and direction of view can be interactively modified with known operating interfaces for the 3D image processing that are connected to the superimposition and fusion computer 23, these interfaces not being shown in FIG. 1. The mixing ratio of 3D ultrasound image data with video image data likewise can be interactively modified.

In the above-described way, thus, an intra-operatively obtained video image from the inside of the body of the patient P generated with the endoscope 2 can be expanded with an intra-operatively generated ultrasound image. In contrast to known systems, no registration is required for the superimposition or fusion of the image data.

If the patient P is moved between the registrations of the ultrasound tomograms with the ultrasound apparatus 1 and the registrations of the video images, the movement of the patient P also is acquired with the navigation system 10. In the exemplary embodiment, the position sensor 15 is applied to the patient P for this purpose. The acquisition of the motion of the patient P makes it possible to also bring pre-operatively obtained 3D ultrasound image datasets, that were registered given an attitude of the patient P that differs from the attitude of the patient P in the minimally invasive surgical intervention, into coincidence with the attitude of the patient P during the intervention. In this way, a pre-operatively obtained and adapted image dataset also can be employed for superimposition or fusion with intra-operatively acquired video image data.

If the video images are distorted compared to the real patient anatomy, as can occur when endoscopes having distorting optics are utilized, then a distortion correction of the video images can be implemented in a known way before the superimposition or fusion of the video image data with the ultrasound data. The video images are free of distortion after the distortion correction.

If the precision of the positions of the 3D ultrasound image dataset and of the video image data determined with the navigation system 10 are inadequate for producing high-quality images with superimposed or fused image data, a fine registration can additionally ensue proceeding from the identified positions of the image data. In this fine registration, standard registration methods can be applied wherein the sought, spatial transformation between the participating image data is determined with the assistance of what are referred to as anatomical landmarks or with the assistance of surfaces or edges. Standard voxel-based registration approach can also be employed for this purpose. As needed, standard registration approaches can also be employed wherein one of the two image datasets is elastically deformed in order to enable an optimum registration. On the basis of this elastic deformation, distortions of the video images caused by the distortion of the endoscope optics also can be corrected. Further, the elastic deformation is of assistance in situations wherein patient repositionings, patient movements and/or patient respiration occur between the registrations of the pre-operatively or intra-operatively acquired 3D ultrasound image data and the registration of the endoscopic video image data.

The superimposition or fusion of 3D ultrasound image data and video image data, moreover, need not necessarily be undertaken by the superimposition and fusion computer 23. Alternatively, the image processing unit 4 of the ultrasound apparatus 1 or the visualization computer 9 can undertake the superimposition or fusion and generate images that comprise superimposed or fused image data.

Differing from the exemplary embodiment described herein, the navigation system 10 need not necessarily be an electromagnetic navigation system. Alternatively, the navigation system can be an optical navigation system, a navigation system based on ultrasound waves or some other known navigation system.

Further, the present invention is not limited to the fusion or superimposition of a 3D image dataset with video image data. Alternatively, 2D image datasets and video image data can be superimposed on one another or fused with one another.

Moreover this, the first systems need not necessarily be an ultrasound apparatus. Alternatively, the first system can be an x-ray apparatus, for example a C-bar x-ray apparatus, or a computed tomograph apparatus or a magnetic resonance apparatus. All of these types of equipment allow image datasets to be generated whose attitude relative to a video image can be identified with the assistance of a navigation system.

Instead of an endoscope, a laparoscope provided with optical means for image pickup or a catheter can be employed as the second system.

The invention was described above with reference to the example of a medical system, but is not limited to the field of medicine.

Although modifications and changes may be suggested by those skilled in the art, it is the intention of the inventor to embody within the patent warranted hereon all changes and modifications as reasonably and properly come within the scope of his contribution to the art.

We claim as our invention:

1. A system for generating an image, comprising:
   a first system for acquiring an image dataset from a subject;
   a second system for obtaining a video image of the subject;
   a unit for generating first position information comprising a position of the first system during acquisition of said image dataset and a position of the second system while obtaining said video image;
   a unit for obtaining second position information comprising a position of the image dataset and a position of the video image; and
   a computer for combining said image data and said video image in a combining operation selected from the group consisting of super-imposition and fusion, using said first position information and said second position information.

2. A system as claimed in claim 1 wherein said unit for generating first position information also identifies a position of the subject and includes said position of the subject in said first position information.

3. A system as claimed in claim 1 wherein said unit for generating first position information is a navigation system.

4. A system as claimed in claim 1 wherein said first system acquires a 3-D image dataset as said image dataset.

5. A system as claimed in claim 1 wherein said first system is an x-ray system.

6. A system as claimed in claim 1 wherein said first system is an ultrasound system.

7. A system as claimed in claim 1 wherein said second system is selected from the group consisting of an endoscope, a laparoscope, and a catheter.

8. A system as claimed in claim 1 wherein said first system acquires a medical image dataset as said image dataset and wherein said second system obtains a video image of an internal region of the subject, and wherein said computer combines said medical image dataset and said video image to produce a medical diagnostic image.

9. A method for generating an image, comprising the steps of:
   acquiring an image dataset of a subject with a first system;
   obtaining a video image of the subject with a second system;
   generating first position information comprising a position of said first system during acquisition of said image dataset and a position of the second system while said video image is obtained;
   generating second position information comprising a position of the image dataset and a position of the video image;
   combining data in said image dataset and data in said video image in a combining operation selected from the group consisting of super-imposition and fusion, using said first position information and said second position information, to produce combined data; and
   generating an image from said combined data.

10. A method as claimed in claim 9 comprising the additional step of determining a position of the subject and including the position of subject in said first position information.

11. A method as claimed in claim 9 comprising generating said first position information with a navigation system.

12. A method as claimed in claim 9 comprising acquiring a 3-D image dataset with said first system as said image dataset.

13. A method as claimed in claim 9 comprising employing an x-ray system as said first system.

14. A method as claimed in claim 9 comprising employing an ultrasound system as said first system.

15. A method as claimed in claim 9 comprising selecting said second system from the group consisting of an endoscope, laparoscope and a catheter.

16. A method as claimed in claim 9 comprising subjecting said video image to a geometrical distortion correction before combining said data in said image data with the data in the video image.

17. A method as claimed in claim 9 comprising the additional step of conducting a fine registration between the image data of the image dataset and the image data of the video image.

* * * * *